US00PP11249P

United States Patent [19]

Zary

[11] Patent Number: Plant 11,249

[45] Date of Patent: Feb. 29, 2000

[54] FLORIBUNDA ROSE PLANT NAMED 'JACBABL'

[75] Inventor: Keith W. Zary, Thousand Oaks, Calif.

[73] Assignee: Bear Creek Gardens, Inc., Medford, Oreg.

[21] Appl. No.: 09/000,727

[22] Filed: Dec. 30, 1997

[51] Int. Cl.[7] ..... A01H 5/00

[52] U.S. Cl. ..... Plt./150

[58] Field of Search ..... Plt./149, 150, 108, Plt./129

*Primary Examiner*—Howard J. Locker

*Attorney, Agent, or Firm*—Klarquist Sparkman Campbell Leigh & Whinston, LLP

[57] ABSTRACT

Floribunda rose plant having a compact, well-branced habit of growth; small, many petalled flowers borne in clusters; small, dark green, semi-glossy foliage which is resistant to powdery mildew and rust.

1 Drawing Sheet

The present invention relates to a new and distinct variety of rose plant of the floribunda class which was originated by me by crossing the variety 'DICquiet', (U.S. Plant Pat. No. 8,900), with the variety 'KORfullwind', (U.S. Plant Pat. No. 8,872).

The primary objective of this breeding was to produce a new rose variety having the disease resistance and well-branched habit of the female parent combined with the disease resistance, glossy foliage, and spreading habit of the male parent. This cross was primarily designed to produce a low growing, well-branched, spreading floribunda. The objective was substantially achieved, along with other desirable improvements, as evidenced by the following unique combination of characteristics that are outstanding in the new variety and that distinguish it from its parents, as well as from all other varieties of which I am aware:

1. Well-branched, low growing, upright but spreading habit;
2. Small, many petalled flowers, borne in clusters;
3. Small, dark green, semi-glossy foliage;
4. Resistance to rust and powdery mildew.

JACbabl is a small, compact spreading floribunda. As the flowers open on the terminal of a branch, there is rapid bud break behind the flowers producing new flowers on short branches very quickly.

Asexual reproduction of this new variety by softwood cuttings, as performed at Wasco and Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'DICquiet' (U.S. Plant Pat. No. 8,900).

*Pollen parent.*—'KORfullwind' (U.S. Plant Pat. No. 8,872).

Classification:

*Botanical.*—Rosa hybrida.

*Commercial.*—Floribunda.

FLOWER

Observations made from specimens grown in a garden environment at Somis, Calif. from January, 1996–Spetember, 1997.

Blooming habit: Continuous.

Bud:

*Size.*—Three quarters of an inch long when the petals start to unfurl.

*Form.*—The bud form is short, globular.

*Color.*—When sepals first divide, bud color is Red Group 53A. When half blown, the upper and lower sides of the petals are Red Group 53B.

*Sepals.*—Color: Green group 138B. Surface texture: Covered with fine hairs. There are three lightly appendaged sepals. There are two unappendaged sepals with hairy edges.

*Receptacle.*—Color: Yellow-Green Group 146B. Shape: Funnel. Size: Small (¼" long×3/16" wide). Surface: Smooth.

*Peduncle.*—Length: Short (1½"). Surface: Smooth and glandular. Color: Light green. Strength: Stiff, erect and slender.

Bloom:

*Size.*—Small. Average open size is two to two and one-half inches.

*Borne.*—Singly and several together in flat clusters.

*Stems.*—Short (six to eight inches).

*Form.*—When first open: Cupped. Permanence: Flattens, all petals curl with some quilling.

*Petalage.*—Number of petals under normal conditions: 50–60.

*Color.*—The upper sides of the petals are Red Group 53B. The reverse sides of the petals are Red Group 53B., The base of each petal has a small (3/16"×3/16") Yellow Group 4C half moon at the point of attachment. The major color on the upper side is Red Group 53B.

*Variegations.*—There are occasional greenish-white streaks on the guard petals and on the petaloids in the center of the flower.

*Discoloration.*—At the end of the first day: No change. At the end of the thrid day: No change. By day four or five there is a general fading to Red Group 53C then to Red Group 53D.

*Fragrance.*—Slight.

Petals:

*Texture.*—Thick.

*Shape.*—Deltoid.

*Form.*—Tips slightly recurved, edges slightly quilled.

*Arrangement.*—Imbricated. Petaloids in the center are many.

*Persistence.*—Drop off cleanly.

*Lastingness.*—On the plant: Fair (five days). As a cut flower: Not tested.

Reproductive parts:

*Anthers.*—Size: Medium. Quantity: Few. Color: Yellow. Arrangement: Regular around styles, mixed with petaloids.

*Filaments.*—Color: Yellow.

*Pollen.*—Color: Gold yellow.

*Styles.*—Color: Greenish-white.

*Stigmas.*—Color: Greenish-white.

Plant:

*Form.*—Bush.

*Growth.*—Vigorous; branching; compact; spreading. 'JACbabl' growing on its own roots will be 24"–28" tall and 24"–30" wide after one full season of growth, without pruning, in Somis, Calif.

Foliage:

*Number of leaflets on normal mid-stem leaves.*—Five or seven.

*Size.*—Small (4"×2½").

*Quantity.*—Abundant.

*Color.*—New foliage: Upper and Lower surfaces, Greyed-Red Group 178A. Old foliage: Upper surface: Green Group 137A. Lower surface: Green Group 137C, except young, fully expanded leaves that retain red pigment for one to two weeks.

*Shape.*—Pointed oval.

*Texture.*—Upper side: Leathery, semi-glossy.

*Edge.*—Serrated.

*Serration.*—Single, small.

*Petiole rachis.*—Color: Reddish, turning green at maturity.

*Petiole underside.*—Smooth with occasional prickles.

*Stipules.*—Short (¼"); serated, bearded.

*Disease resistance.*—Resistant to mildew and rust under normal growing conditions at Somis, Calif.

Wood:

*New wood.*—Color: Reddish but very quickly turns green. Bark: Smooth.

*Old wood.*—Color: Green. Bark: Smooth.

Prickles:

*Quantity.*—On main canes from base: Ordinary. On laterals from main canes: Ordinary.

*Form.*—Short (3/16"); straight to hooked slightly downward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by a compact, well-branched, spreading habit of growth; small, many petalled flowers borne in clusters; resistance to powdery mildew and rust; and small, dark green, semi-glossy foliage.

* * * * *

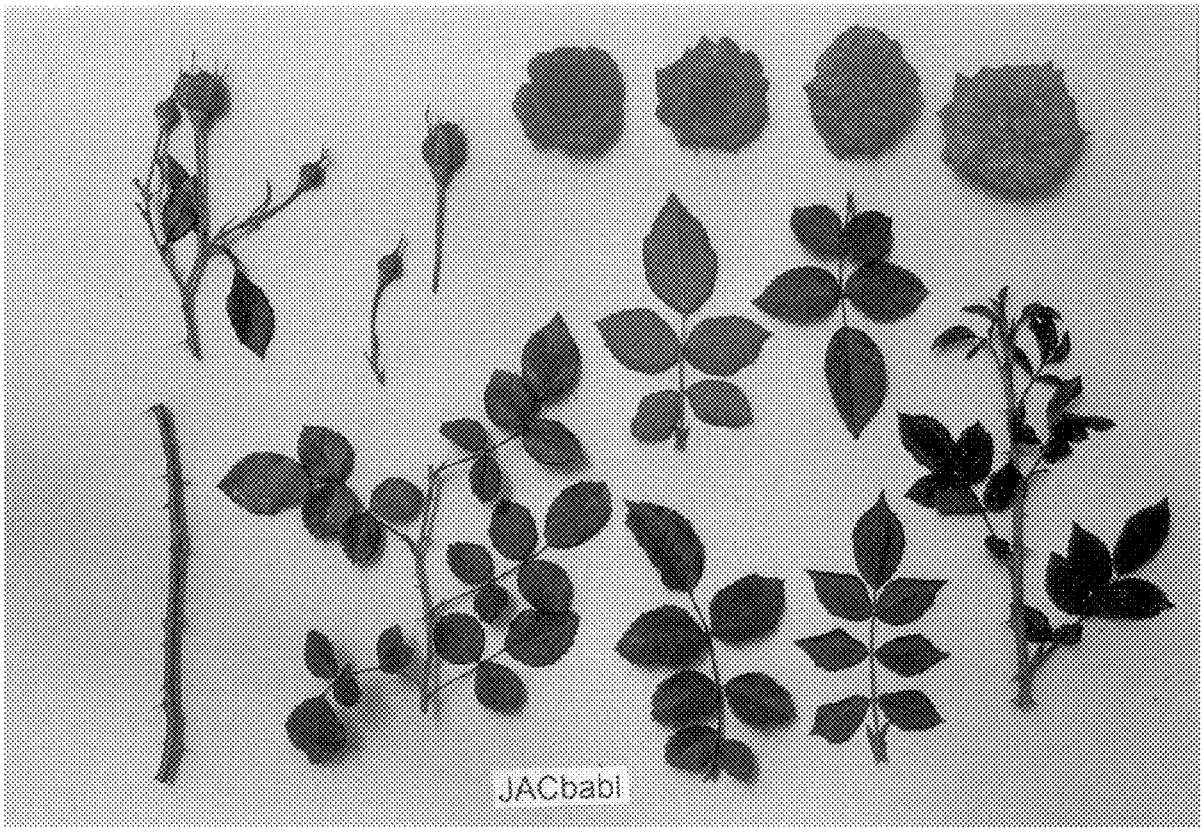
JACbabl

UNITED STATES PATENT AND TRADEMARK OFFICE

CERTIFICATE OF CORRECTION

PATENT NO. : PP11,249
DATED : February 29, 2000
INVENTOR(S) : Keith W. Zary, Ph.D.

It is certified that error appears in the above-identified patent and that said Letters Patent is hereby corrected as shown below:

In the Abstract:
Line 1 reads "well-branced". It should read --well-branched--.

In the Specification:
Column 1,
Line 22, reads "floribunda". It should read --floribunda that is always in flower--.

Column 2,
Line 5, reads "September". It should read --September--.
Line 38, reads "53B.,". It should read --53B.--.

Signed and Sealed this

Third Day of July, 2001

Nicholas P. Godici

*Attest:*

*Attesting Officer*

NICHOLAS P. GODICI
*Acting Director of the United States Patent and Trademark Office*